United States Patent [19]

Franz et al.

[11] 4,110,100

[45] Aug. 29, 1978

[54] PHOSPHINYLMETHYLIMINO-ACETIC ACID N-OXIDE COMPOUNDS AND THE SUCROSE INCREASING USE THEREOF

[75] Inventors: John E. Franz, Crestwood, Mo.; Reuven M. Sacher, Kraainem, Belgium

[73] Assignee: Monsanto Company, St. Louis, Mo.

[21] Appl. No.: 823,908

[22] Filed: Aug. 12, 1977

[51] Int. Cl.$^2$ ............................ C07F 9/30; C07F 9/48; A01N 9/36
[52] U.S. Cl. ........................................ 71/86; 260/502.5
[58] Field of Search ........................... 260/502.5; 71/86

[56] References Cited

U.S. PATENT DOCUMENTS

| | | | |
|---|---|---|---|
| 3,394,172 | 7/1968 | Schiefer | 260/502.5 |
| 3,556,762 | 1/1971 | Hamm | 71/86 |
| 3,853,530 | 12/1974 | Franz | 71/86 |
| 4,047,927 | 9/1977 | Gaertner et al. | 71/86 |

OTHER PUBLICATIONS

Frank, "Chem. Reviews", vol. 61 (Aug. 1961), pp. 389–424.

*Primary Examiner*—Joseph E. Evans
*Attorney, Agent, or Firm*—William T. Black; Donald W. Peterson

[57] ABSTRACT

This disclosure relates to phosphinylmethylimino-acetic acid N-oxide compounds and to sucrose increasing compositions and methods. The compounds and compositions are useful as sucrose increasing agents when applied to sugar cane prior to harvesting.

23 Claims, No Drawings

PHOSPHINYLMETHYLIMINO-ACETIC ACID N-OXIDE COMPOUNDS AND THE SUCROSE INCREASING USE THEREOF

This invention relates to novel phosphinylmethylimino-acetic acid N-oxide compounds and to sucrose increasing compositions and methods. The compounds and compositions are useful as sucrose increasing agents when applied to growing sugar cane prior to the harvesting of such sugar cane.

The phosphinylmethyliminoacetic acid N-oxide compounds of this invention are those having the formula

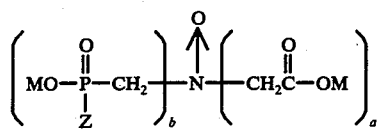
(I)

wherein Z is hydrogen, lower alkyl, phenyl or a

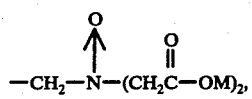

M is hydrogen or an agriculturally acceptable salt-forming cation and $a$ and $b$ are the integers 1 or 2, the sum of $a + b$ being 3, provided that when Z is other than hydrogen, lower alkyl or phenyl, then $a$ is equal to 2.

By agriculturally acceptable cation is meant those cations which would not render the compounds unsuitable for agricultural use, e.g., those cations which are not unacceptably unstable or toxic to mammals. Such agriculturally acceptable cations are preferably an alkali metal, and alkaline earth metal, an ammonium group including heterocyclic ammonium or a hydrazine cation. Especially preferred are an alkali metal, an alkaline earth metal or an ammonium cation of the formula $^+NHRR_1R_2$ wherein R, $R_1$ and $R_2$ are independently hydrogen or hydrocarbon ($C_1$–$C_{20}$) radicals which may be substituted by a —$NR_3R_4$ group wherein $R_3$ and $R_4$ are independently alkyl ($C_1$–$C_{20}$) or an $OR_5$ group wherein $R_5$ is hydrogen, alkyl ($C_1$–$C_{10}$) or phenyl. Cations particularly suitable are sodium, potassium or an ammonium cation of the formula $^+NHR'R_1'R_2'$ wherein R', $R_1'$ and $R_2'$ are each independently hydrogen or alkyl ($C_1$–$C_4$).

Representative of the $C_1$–$C_{20}$ hydrocarbon groups represented by R, $R_1$ and $R_2$ are alkyl groups such as methyl, ethyl, isopropyl, t-butyl, octadecyl and their isomers, alkenyl groups such as vinyl, allyl, undecenyl, octadecenyl and the like, alkynyl groups such as ethynyl, propynyl and the like, aryl such as phenyl, naphthyl, tolyl, xylyl and the like, aralkyl such as benzyl, phenethyl and the like.

The N-oxide compounds of this invention are produced by the following general procedure. A phosphinylmethylimino-acetic compound of the formula

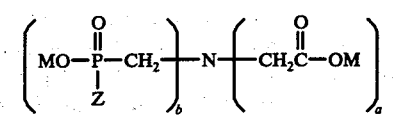
(II)

wherein $a$, $b$, M and Z as are above defined, is dissolved in a suitable solvent and hydrogen peroxide is added while maintaining the temperature at from about 0° to 50° C. (preferably 20° to 35° C.) whereby the hydrogen peroxide oxidizes the phosphinylmethyliminoacetic acid compound of Formula II to the N-oxide compound of Formula I.

Solvents suitable for conducting the process include water, dilute sulfuric acid and organic acids such as perfluoroacetic, pentafluoropropionic, heptafluorobutyric, acetic acid, formic acid, propionic acid and the like.

The N-oxide product is generally recovered by precipitation from the reaction medium or by concentrating the reaction medium to dryness and then recrystallizing the residue from a solvent.

EXAMPLE 1

A mixture of N-phenylphosphinylmethyliminodiacetic acid (4.3 g, 0.015 mole), trifluoroacetic acid (25 ml) and hydrogen peroxide (2 ml, 30%, 0.018 mole) was stirred at room temperature for approximately 19 hours to yield a clear yellow solution. The solution was concentrated under reduced pressure to yield a yellow gummy residue. The residue was mixed with tetrahydrofuran (25 ml) and allowed to stand overnight to yield a white solid (4.8 g). The latter product was recovered by filtration and recrystallized from acetic acid. The recrystallized solid was then washed with acetic acid and diethyl ether and dried. The purified product weighed 3.4 gm (0.011 mole, 75% yield) and had a melting point of 150° C. with decomposition. The white solid was identified as N-phenylphosphinylmethyliminodiacetic acid N-oxide and had the following analysis.

Calculated: C, 43.57; H, 4.65; N, 4.62; P, 10.22.
Found: C, 43.47; H, 4.66; N, 4.51; P, 10.41.

EXAMPLE 2

N-Methylphosphinylmethyliminodiacetic acid (2.25 g, 0.01 mole) was dissolved in hot trifluoroacetic acid (25 ml) and the solution cooled to room temperature. The solution was agitated as 30% aqueous hydrogen peroxide (2.25 g, 0.02 mole) was added. The reaction mixture was stirred for approximately ½ hour and then was concentrated under vacuum (<50°, 30 mmHg) with careful warming. The resulting powder was dissolved in ethanol and the ethanol solution decanted from a small amount of a solid. The solution then was evaporated to dryness and the residual white powder washed with tetrahydrofuran and diethyl ether. After being dried in a vacuum desiccator, the weight of the white powder was 3.2 g. The product was identified as N-methylphosphinylmethyliminodiacetic acid N-oxide hemihydrate, had a melting point of 80° C. with decomposition and had the following analysis.

Calculated: C, 28.80; H, 5.25; N, 5.60; P, 12.38.
Found: C, 29.41; H, 5.41; N, 5.65; P, 12.65.

EXAMPLE 3

N,N-Bis(hydroxyphosphinylmethyl)iminoacetic acid, monosodium salt (2.55 g, 0.01 mole) was dissolved in water (20 ml) and sodium hydroxide (0.8 gm, 0.02 mole) was added to form a solution of the trisodium salt. The solution of the trisodium salt was mixed with 30% hydrogen peroxide (1.2 g, 0.01 mole) and allowed to stand at room temperature for 6 days. The reaction solution was concentrated on a warm water bath under reduced pressure (~30 mmHg) to yield a solid residue.

The residue was mixed with ethanol and stirred at room temperature. The precipitated product was collected, washed with ethanol and diethyl ether and then was dried at room temperature in a vacuum desiccator at about 30 mmHg for 6 days. The white powder (3.0 g, 86% yield) had a melting point of 140° to 145° C. with decomposition and was identified as N,N-bis(hydroxyphosphinylmethyl)glycine N-oxide, trisodium salt, dihydrate which had the following analysis.

Calculated: C, 13.76; H, 3.47; N, 4.01; P, 17.75. Found: C, 14.04; H, 3.45; N, 3.97; P, 17.57.

EXAMPLE 4

Phosphinico(methylenenitrilo)tetraacetic acid

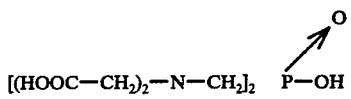

(3.6 g, 0.01 mole), water 20 ml and sodium hydroxide (2.0 gm, 0.05 mole) were mixed to form the pentasodium salt of the acid. This solution was then mixed with 30% hydrogen peroxide (4.5 g, 0.04 mole) and allowed to stand for 24 hours. An additional 2.3 g (0.02 mole) of 30% hydrogen peroxide was added and the mixture allowed to stand overnight. N.m.r. analysis indicated that the reaction was not complete. Therefore, an additional 1.2 g of 30% hydrogen peroxide was added and the solution allowed to stand at room temperature for 48 hours. Nuclear magnetic resonance (nmr) spectral analysis now indicated that the reaction was essentially complete. The reaction mixture was concentrated under reduced pressure (50° C. at 30 mmHg) and the residue was diluted with ethanol. The precipitated product was ground under ethanol and the crude white powder obtained was washed with ethanol, then diethyl ether and air-dried. The white solid was then dried in a vacuum dessicator (about 30 mmHg) for 6 days. The resulting powder (5.2 g) had a melting point of 100° to 110° C. with decomposition. Analysis of the white powder showed it to be 93% N,N'-(hydroxyphosphinylidenedimethylene)-bis(iminodiacetic acid)-N,N'-dioxide, pentasodium salt, tetrahydrate. Elemental analysis was as follows.

Calculated: C, 19.60; H, 3.30; N, 4.57; P, 5.05; Na, 18.72. Found: C, 19.73; H, 3.25; N, 4.35; P, 4.91; Na, 18.80.

EXAMPLE 5

To a solution of N-hydroxyphosphinylmethyliminodiacetic acid (2.1 g, 0.01 mole) in water was added sodium hydroxide (1.2 g, 0.03 mole) in 20 ml of water to prepare the trisodium salt. 30% hydrogen peroxide (1.2 g, 0.01 mole) was then added with stirring and the solution stored at ambient temperature for 6 days. The colorless solution was concentrated on a warm water bath at reduced pressure (20 mmHg) to yield a gum. The gum was further concentrated at 0.5 mmHg in a warm water bath until a white powder (3.0 g) was obtained which was identified as N-hydroxyphosphinylmethyliminodiacetic acid N-oxide, trisodium salt, trihydrate having a melting point of 120° C. with decomposition and the following analysis.

Calculated: C, 17.30; H, 3.77; N, 4.04. Found: C, 17.25; H, 3.50; N, 3.81.

EXAMPLE 6

In determining the regulatory effects of compounds of this invention on sugar cane, it should be noted that the appropriate rate of application can vary from about 0.56 kilograms per hectare to about 5.6 kilograms per hectare. Depending upon local cultural practices, sugar cane is grown for from about 9 to about 30 months before harvest, and it is thus necessary to consider both the chronological age and the maturity stage of the cane in rate determinations. Application of the treatment to the cane is generally made from about 2 to 10 weeks prior to the scheduled harvest date. Preferably, such applications are made from 3 to 7 weeks before said date.

In this test individual sugar cane stalks are treated with compounds of this invention about 4-5 weeks before harvest. To avoid sampling errors, older cane, preferably 13-23 months old, is employed in the tests. For each compound employed, at least five stalks are used, processed and the total values obtained are averaged for each stalk. In order to improve the accuracy of the analyses, only the terminal 15 joints of each stalk are used. An identical number of untreated sugar cane stalks of the same age are similarly processed to provide a control. A comparison of the values obtained for the treated cane with the control sample provides a convenient means of determining the regulatory effectiveness of these compounds.

The analyses are carried out by the press method developed by T. Tanimoto and reported in Hawaiian Planters' Record, Volume 57, pp. 133-150 (1964). The data are expressed as Juice Purity and Pol percent Cane. Pol percent Cane is a polarimetric determination and equals the percentage of sucrose if it is the only substance in the solution which will rotate the plane of polarized light. A determination of Pol percent Cane is considered by those skilled in the art as an effective means of determining the sucrose content of sugar cane juice.

A 38 mg. sample of each compound employed is dissolved in a small amount of water which contains a small amount of a surface-active agent. The resultant solution is then applied to the tip of each of the stalks to be tested with the exception of the untreated controls. At 4 or 5 weeks after treatment, the plants are harvested, and the top 15 joints of each stalk of a treated group are removed, combined and analyzed as described.

In order to convert a change in Pol percent Cane into a corresponding change in the quantity of sugar obtained, it is first necessary to know the average normal yield of sugar in the area under test. Here, the tests are carried out in a region where about 101.8 to 112 metric tons of cane are harvested per hectare, and about 10.18 metric tons of sugar are obtained from this quantity of cane. With this average normal yield of 10.18 metric tons per hectare, an increase of just 1.0 Pol percent Cane translates to an increase of 224 kilograms of sugar per hectare.

The results obtained in tests with various compounds listed above are as follows:

| | HARVEST | | | |
|---|---|---|---|---|
| | Four Weeks | | Five Weeks | |
| Compound of Example | Juice Purity | Pol % Cane | Juice Purity | Pol % Cane |
| 1 | 83.33 | 12.31 | 85.83 | 14.86 |
| 4 | 85.83 | 12.66 | 87.12 | 14.26 |
| 5 | 87.12 | 13.48 | 84.94 | 13.09 |
| Control | 79.77 | 9.67 | 81.72 | 11.38 |

| | HARVEST | | | |
|---|---|---|---|---|
| | Four Weeks | | Five Weeks | |
| Compound of Example | Juice Purity | Pol % Cane | Juice Purity | Pol % Cane |
| 3 | 64.62 | 7.27 | 74.78 | 9.56 |
| Control | 64.25 | 6.63 | 65.99 | 6.85 |
| 3 | 72.01 | 8.47 | 80.02 | 10.97 |
| Control | 69.93 | 7.35 | 54.64 | 4.86 |

The active ingredients of this invention can, of course, be applied to the sugar cane plants in the free acid form shown in the formula above. Alternatively, such ingredients can be applied in the form of an agriculturally acceptable metal or amine salt. It is often found that a salt form improves such desirable features as stability or solubility, and these salts are prepared by adding an appropriate amount of a base or basic carbonate or amine to a water solution of the free acid. Both mono and divalent metals can be employed at the salt-forming cation, while the amines can be primary, secondary or tertiary. Particularly preferred salts are those of the alkali metals, ammonia and the lower aliphatic hydrocarbon amines.

An active ingredient of this invention can be conveniently applied to the plants as an aqueous solution or suspension. For example, a liquid composition may be applied from a boom-spray, or a solid dust composition where the active component is diluted with an inert solid such as clay can be flown on the plants from an aircraft. Suitable liquid compositions include surfactants such as those enumerated in U.S. Pat. Nos. 3,224,865 and 3,245,775. Preferred surface-active agents of this invention are of the non-ionic type such as alkyl phenoxy poly(ethyleneoxy)ethanols, polyethylene oxide adducts of fatty and resin acids, and long chain alkyl mercaptan adducts with ethylene oxide.

A particularly preferred carrier for the acids or salts of this invention is water with about 0.1 to 2.0 percent by weight of surfactant added thereto. Alternatively, the aqueous carrier can be replaced by a non-toxic mineral oil as such, or as an oil-in-water or water-in-oil emulsion. It has been found convenient to apply the compositions to the plants in the form of aqueous solutions, suspensions or emulsions, the dilution being such that a spray volume of from about 65.5 to 187 liters of liquid per hectare will contain the desired dosage of active ingredient. It will be recognized, however, the higher or lower total spray volumes can be beneficially employed depending upon, the particular dispensing apparatus and other factors well understood by those skilled in the art. The exact amount of active ingredient to be employed is dependent upon such factors as the cane variety and stage of development thereof, and the environmental conditions, as well as the specific aminomethylenephosphinic acid N-oxide employed. In general, the active ingredients are employed in effective sucrose increasing amounts of from about 0.56 to about 5.6 kilograms per hectare. It should be understood that the amount of active ingredient employed must be sufficient to increase the sucrose deposition in the treated plants without producing a herbicidal or killing effect on such plants. It is believed that those skilled in the art can readily determine from the teachings of this specification, including examples, the appropriate application rates.

While the invention has been described herein with regard to certain representative examples for purpose of illustrating its practice, it is not to be construed as limited thereto. Those skilled in the art will readily recognize the variations and modifications which can be made without departing from the spirit and scope of the invention.

What is claimed is:

1. A compound of the formula

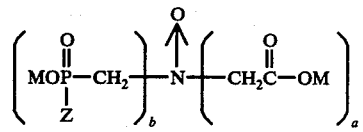

wherein Z is hydrogen, lower alkyl, phenyl or a

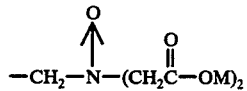

and M is hydrogen or an agriculturally acceptable salt-forming cation, $a$ and $b$ are the integers 1 or 2, the sum of $a + b$ being 3, provided that when Z is other than hydrogen, lower alkyl or phenyl, $a$ is equal to 2.

2. A compound of claim 1 wherein Z is

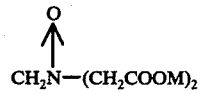

wherein M is hydrogen or an agriculturally acceptable salt-forming cation.

3. A compound of claim 1 wherein Z is hydrogen.
4. A compound of claim 1 wherein Z is phenyl.
5. A compound of claim 4 which is N-phenylphosphinylmethyliminodiacetic acid N-oxide.
6. A compound of claim 3 which is N,N-bis(hydroxyphosphinylmethyl)glycine N-oxide trisodium salt.
7. A compound of claim 3 which is N-hydroxyphosphinylmethyliminodiacetic acid trisodium salt N-oxide.
8. A compound of claim 2 which is N,N'-(hydroxyphosphinylidenedimethylene)-bis(iminodiacetic acid) N,N'-dioxide.
9. A method for increasing the sucrose content of sugar cane plants which comprises applying to said plants, from about 2 to 10 weeks prior to harvest, an effective amount of a compound of claim 1.
10. A method for increasing the sucrose content of sugar cane plants which comprises applying to said plants, from about 2 to 10 weeks prior to harvest, an effective amount of a compound of claim 3.
11. A method for increasing the sucrose content of sugar cane plants which comprises applying to said plants, from about 2 to 10 weeks prior to harvest, an effective amount of a compound of claim 4.
12. A method for increasing the sucrose content of sugar cane plants which comprises applying to said plants, from about 2 to 10 weeks prior to harvest, an effective amount of a compound of claim 5.

13. A method for increasing the sucrose content of sugar cane plants which comprises applying to said plants, from about 2 to 10 weeks prior to harvest, an effective amount of a compound of claim 6.

14. A method for increasing the sucrose content of sugar cane plants which comprises applying to said plants, from about 2 to 10 weeks prior to harvest, an effective amount of a compound of claim 7.

15. A method for increasing the sucrose content of sugar cane plants which comprises applying to said plants, from about 2 to 10 weeks prior to harvest, an effective amount of a compound of claim 8.

16. A composition for application to sugar cane plants to increase the sucrose content which comprises a solution or suspension of an effective amount of a compound of the formula

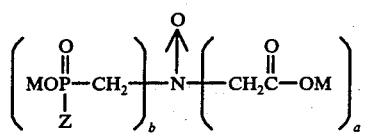

wherein Z is hydrogen, lower alkyl, phenyl or a

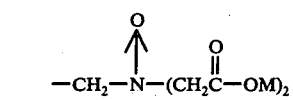

and M is hydrogen or an agriculturally acceptable salt-forming cation, $a$ and $b$ are the integers 1 or 2, the sum of $a + b$ being 3, provided that when Z is other than hydrogen, lower alkyl or phenyl, $a$ is equal to 2, in an agriculturally acceptable diluent.

17. The composition of claim 16 wherein Z is hydrogen.

18. The composition of claim 16 wherein Z is phenyl.

19. The composition of claim 16 wherein Z is

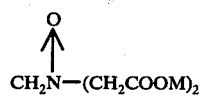

wherein M is hydrogen or an agriculturally acceptable cation.

20. The composition of claim 18 wherein the compound is N-phenylphosphinylmethyliminodiacetic acid N-oxide.

21. The composition of claim 17 wherein the compound is N-carboxymethyliminodimethylphosphonic acid trisodium salt N-oxide.

22. The composition of claim 17 wherein the compound is N-hydroxyphosphinylmethyliminodiacetic acid trisodium salt N-oxide.

23. The composition of claim 19 wherein the compound is N,N'-(hydroxyphosphinylidenedimethylene)-bis(iminodiacetic acid)-N,N'-dioxide.

* * * * *